United States Patent
Estrada Garcia et al.

(10) Patent No.: US 9,603,900 B2
(45) Date of Patent: *Mar. 28, 2017

(54) USE OF PACAP FOR THE TREATMENT OF VIRAL INFECTIONS IN AQUATIC ORGANISMS

(71) Applicant: Centro de Ingenieria Genetica y Biotecnologia, Havana (CU)

(72) Inventors: Mario Pablo Estrada Garcia, Havana (CU); Juana Maria Lugo Gonzalez, Artemisa (CU); Yamila Carpio Gonzalez, Havana (CU); Carolina Tafalla Pineiro, Madrid (ES)

(73) Assignee: CENTRO DE INGENIERIA GENETICA Y BIOTECNOLOGIA, Havana (CU)

( * ) Notice: Subject to any disclaimer, the term of this patent is extended or adjusted under 35 U.S.C. 154(b) by 0 days.

This patent is subject to a terminal disclaimer.

(21) Appl. No.: 14/839,114

(22) Filed: Aug. 28, 2015

(65) Prior Publication Data
US 2016/0030519 A1    Feb. 4, 2016

Related U.S. Application Data

(62) Division of application No. 13/989,921, filed as application No. PCT/CU2011/000008 on Nov. 30, 2011, now Pat. No. 9,119,830.

(30) Foreign Application Priority Data

Dec. 1, 2010 (CU) .................................. 2010-0233

(51) Int. Cl.
| | |
|---|---|
| *A61K 9/08* | (2006.01) |
| *A61K 38/22* | (2006.01) |
| *A61K 31/7056* | (2006.01) |
| *A61K 9/00* | (2006.01) |
| *A61K 9/51* | (2006.01) |

(52) U.S. Cl.
CPC ........ *A61K 38/2278* (2013.01); *A61K 9/0019* (2013.01); *A61K 9/0056* (2013.01); *A61K 9/08* (2013.01); *A61K 9/5153* (2013.01); *A61K 31/7056* (2013.01); *A61K 38/22* (2013.01)

(58) Field of Classification Search
None
See application file for complete search history.

(56) References Cited

U.S. PATENT DOCUMENTS

2009/0176703 A1 * 7/2009 Gonzalez ............... A01K 61/02
514/1.1

OTHER PUBLICATIONS

Moya et al., In Vivo Effect of EICAR (5-ethynyl-l-beta-D-ribofuranosylimidazole-carboxamide) on Experimental Infected Rainbow Trout (Oncorhynchus mykiss) and Coho Salmon (Oncorhynchus kisutch) Fry with Infectious Pancreatic Necrosis Virus, Antiviral Research, vol. 48, No. 2, pp. 125-130 (Nov. 2000).—copy provided with IDS filed Aug. 19, 2013.*
Pathogen, the free medical dictionary accessed Jul. 22, 2016 at URL medical-dictionary.thefreedictionary.com/pathogen, pp. 1-5.*

* cited by examiner

*Primary Examiner* — Julie Ha
*Assistant Examiner* — Kristina M Hellman
(74) *Attorney, Agent, or Firm* — Hoffmann & Baron, LLP

(57) ABSTRACT

The present invention relates to the use of pituitary adenylate cyclase activating polypeptide (PACAP) in the treatment of viral diseases and infectious diseases caused by viruses in aquatic organisms. PACAP, alone or combined with an antiviral molecule, demonstrated its effectiveness by increasing the survival of fish or crustaceans infected by viruses when it was administered orally, by injection or by immersion baths. Furthermore, it was observed that treated organisms keep or increase its weight as compared to infected and non-treated organisms. PACAP or PACAP-containing combinations decreased the viral load in tissues and organs susceptible to viral infections as it was determined by RT-PCR.

11 Claims, 10 Drawing Sheets

USE OF PACAP FOR THE TREATMENT OF VIRAL INFECTIONS IN AQUATIC ORGANISMS

CROSS-REFERENCE TO RELATED APPLICATIONS

This application is a division of U.S. application Ser. No. 13/989,921, filed May 28, 2013, which is a U.S. National Phase of, and Applicants claim priority from, International Application No. PCT/CU2011/000008, filed Nov. 30, 2011, and Cuban Patent Application No. 2010-0233, filed Dec. 1, 2010, all of which are incorporated herein by reference in their entireties.

FIELD OF THE INVENTION

The present invention relates to the field of aquatic biotechnology, particularly with the use of PACAP and PACAP-containing compositions for treating viral infections or infectious diseases caused by viruses in aquatic organisms. It also relates to the use of PACAP in combination with antivirals to treat infections caused by virus.

BACKGROUND OF THE INVENTION

The annual contribution of the aquatic species culture to the total production of fish and shellfish has increased in recent times. However, higher densities imply that these animals live in stress conditions and, in general, they are more susceptible to infections. Disease outbreaks caused by pathogens in aquaculture result in large economic losses and even sometimes produce the removal of certain culture from a specific region.

In salmonids, the infestations caused by the infectious pancreatic necrosis virus (IPNV), the viral hemorrhagic septicemia virus (VHSV), the infectious salmon anemia virus (ISAV) and the infectious hematopoietic necrosis virus (IHNV) are the main causes of disease outbreaks in their culture (Marroqui et al. (2008) Antiviral Research 80: 332-338). For example, it is estimated that Chilean salmon production for the year-end 2010 will fall by 38.7% (from 403 000 tonnes in 2009 until 245 000 tonnes in 2010) as a result of mortality caused by ISAV.

Moreover, the crustaceans are one of the most important economic sectors in global aquaculture, contributing over 10 billion annually. The shrimps in culture are susceptible to a wide variety of pathogens including viruses. It is estimated than in the mid-90 approximately 40% of world production (equivalent to 3 billion U.S. dollars) was lost as a consequence of diseases. Five viruses are the main contributors to these losses: the white spot syndrome virus (WSSV), the yellow head virus (YHV), the taura syndrome virus (TSV), the infectious hematopoietic necrosis virus (IHNNV) and the monodon baculovirus (MBV) (reviewed by Johnson et al. (2008) Vaccine 26: 4885-4992).

Bivalves are an important part of the global shellfish production. These organisms, having the characteristic of being filter feeders, are important virus reservoirs; thus their culture may face epizootics which threat its production. It has been reported mass mortalities of adult's oysters of *Crassostrea angulata* associated with viral infections similar to iridovirus. In addition, other viruses of Herpesviridae, Papovaviridae, Togaviridae, Retroviridae, Reoviridae, Birnaviridae and Picornaviridae families are capable to infect bivalve's cultures. However, due to the absence of cell lines derived from shellfish and the limiting existing molecular tools for these organisms, bivalve virology is still a primitive science based primarily on morphological studies and few experimental studies (reviewed by T. Renault and B. Novoa (2004) Aquat. Living Resour. 17: 397-409).

Antiviral drugs are chemical compounds used to treat infections caused by viruses. The first experimental antivirals were discovered in the early 60's. These were developed based on the "trial" and "error" methodology. However, after the mid 80's, the scene changed dramatically and in recent years many novel antiviral drugs have been developed and registered, mostly for the treatment of the human immunodeficiency virus (HIV). However, since these compounds are not always effective or well tolerated, there are many aspects to be improved. Additional reasons to refine the design and application of these drugs are the emergence of viral resistance or side effects associated with them (De Clercq (2002) Nature Reviews Drug Discovery 1: 13-25). The antiviral drug design has as main targets viral proteins or host cell proteins. The first strategy leads to compounds more specific and less toxic, but with a narrower spectrum of antiviral activity and a greater chance of developing resistance. The second strategy results in discovering antiviral compounds with a broader spectrum of activity, less likely to develop resistance but higher probability to produce cellular toxicity. The strategy of choice depends on the nature of the virus and the potential targets in the virus or in the host cells (De Clercq (2002) Nature Reviews Drug Discovery 1:13-25).

Ribavirin is a broad-spectrum antiviral compound with activity against a wide range of DNA and RNA viruses. It is a nucleoside analogue, which after intracellular phosphorylation, becomes a competitive inhibitor of inosine monophosphate dehydrogenase (IMPDH), a cellular enzyme involved in the synthesis of guanosine monophosphate (GMP) (Graci y Cameron, (2006) Reviews in Medical Virology 16: 49-63; Parker, (2005) Virus Research 107: 165-171). In addition to the inhibition of this enzyme, there are other three mechanisms which have been proposed to explain the antiviral activity of this compound: by direct inhibition of viral RNA polymerase (Toltzis et al. (1988) Antimicrobial Agents and Chemotherapy 32: 492-497), the inhibition of the cap addition at the 5' end of viral messenger RNA (mRNA) (Goswami et al. (1979) Biochemical and Biophysical Research Communications 89: 830-836) and the accumulation of mutations (Graci y Cameron, (2002) Virology 298: 175-180).

Up to now, there are not specific antiviral drugs approved for the treatment of viral diseases in aquatic organisms. In Chile, a subsidiary of Diagnotec SA named Andromaco, developed a new antiviral compound called VIROTOP for the treatment of viral diseases in fish. This antiviral is pending for approval by the "Servicio Agricola y Ganadero" (SAG). However, a significant number of compounds have been evaluated in vitro and in vivo (Hudson et al. (1988) Antiviral Research 9:379-385; Jasher et al. (2000) Antiviral Research 45: 9-17; Kamei and Aoki, (2007) Archives of Virology 152: 861-869; LaPatra et al. (1998) Fish and Shellfish Immunology 8: 435-446; Mas et al. (2006) Antiviral Research 72: 107-115; Micol et al. (2005) Antiviral Research 66: 129-136; Moya et al. (2000) Antiviral Research 48: 125-130), showing various degrees of effectiveness.

The administration of a ribavirin analog, 5-ethynyl-1-β-D-ribofuranosylimidazole-carboxamide (EICAR) has been evaluated in vivo in larvae of salmon coho (*Oncorhynchus kisutch*) and rainbow trout (*Oncorhynchus mykiss*) experimentally infected with IPNV (Moya et al. (2000) Antiviral Research 48: 125-130). Treatment consisted of daily baths in a solution of 0.4 and 0.8 µg/mL of EICAR for two hours during 20 days. The results showed that the survival of the infected groups and treated with EICAR was similar to survival in the groups not infected with the virus. An analysis of viral load in liver and spleen was performed using the technique of reverse transcription chain reaction polymerase (RT-PCR). This analysis demonstrated a decrease in viral load in animals treated with the antiviral. From this study, it was concluded that EICAR is an inhibitor of IPNV replication, so that their use to reduce viral load and prevent fish mortality is a beneficial tool for increasing crops productivity. However, antiviral treatment is not useful for breeding selection, because infected and treated fish still carry the virus and can transmit it to offspring. On the other hand, it has observed that one of the damage caused by some viral infections is the weight loss in infected fish (Wolf (1986) The fish viruses In: Espinosa de los Monteros, J., Labarta, U. (Eds.), Patología en Acuicultura. Industrias gráficas, España, SL, pp. 93-95; Moya et al. (2000) Antiviral Research 48: 125-130).

An additional advantage of the use of antivirals is that this weight loss is much lower in fish treated. This effect was most evident in trout than in salmo coho (Moya et al. (2000) Antiviral Research 48: 125-130).

Pituitary adenylate cyclase activating polypeptide (PACAP) belongs to the superfamily of secretin/glucagon/vasoactive intestinal peptide. This peptide was first isolated from bovine hypothalamus in 1989. It was demonstrated its ability to stimulate the secretion of growth hormone through activation of adenylate cyclase and subsequent stimulation of the production of adenosine monophosphate (cAMP) (Miyata et al (1989) Biochem Biophys Res Commun 164 567-574). PACAP is a multifunctional neuropeptide that plays important roles as neurotransmitter, neuromodulator and vasodilator in mammals (Arimura A. (1998) Japanese Journal of Physiology 48:301-31). It has been demonstrated its function in cell division regulation, differentiation and cell death (Sherwood et al. (2000) Endocrine Review 21: 619-670). This peptide exists in two different molecular variants: 27 aa (PACAP27) and 38 aa (PACAP38) (Miyata et al. (1990) Biochemical and Biophysical Research Communications 170:643-8). The effects of PACAP are exerted through a family of three VIP/PACAP receptors that belong to the secretin G-protein-coupled receptor. VPAC-1 and VPAC-2 receptors exhibit similar affinities for the two neuropeptides, VIP and PACAP, whereas PACAP receptor (PAC-1) exhibits a higher affinity for PACAP than for VIP (Vaudry et al. (2000) Pharmacol Rev 52: 269-324). PACAP is widely distributed in the mammalian brain, mainly in the hypothalamus, the paraventricular and dorsamedial nuclei of the thalamus, in the septum, the cerebral cortex, the amygdala, the hippocampus and the cerebellum (Montero et al. (2000) Journal of Molecular Endocrinology 25: 157-168). The most abundant variant in the central nervous system and peripheral tissues is PACAP38. The studies performed in mammals showed the presence of PACAP also in gonads (Shioda et al. (1994) Endocrinology 135: 818-825), adrenal glands (Arimura et al. (1991) Endocrinology 129: 2787-2789), parathyroid glands (Vaudry et al. (2000) Pharmacol Rev 2000; 52: 269-324), endocrine pancreas (Arimura y Shioda (1995) Neuroendocrinology 16: 53-88) and the gastrointestinal tract (Arimura et al. (1991) Endocrinology 129: 2787-2789; Vaudry et al. (2000) Pharmacol Rev 52: 269-324; Hannibal et al. (1998) Cell. Tissue. Res. 291: 65-79).

PACAP and its receptors expression in immune cells have been only partially elucidated (Gaytan et al. (1994) Cell Tissue Res 276:223-7; Abad et al. (2002) NeuroImmunoModulation 10:177-86). In mammals, it has been observed constitutive expression of VPAC-1 receptor in peripheral blood lymphocytes in humans and mice lymphocytes and macrophages, whereas the expression of VPAC-2 is inducible in these cells. Moreover, it has been observed constitutive expression of PAC-1 receptor in rat peritoneal macrophages and human myelomonocytic cell line THP-1. Additionally, it has been reported PACAP expression in thymocytes, different subtypes of T cells, B cells, splenocytes and lymph nodes in rats (Delgado et al. (2001) J Biol Chem 276:369-80; Pozo et al. (2003) Trends Mol Med 9:211-7).

In fish, PACAP has been described in the central (especially hypothalamus, brain and spinal cord) and peripheral nervous system, innervating eyes, pituitary gland, respiratory tract, salivary glands, gastrointestinal tract, reproductive tract, pancreas and urinary tract (Sherwood et al. (2000) Endocrine Review 21: 619-670).

PACAP inhibits the spontaneous apoptosis of thymocytes in rats (Delgado. (1996) Blood 87: 5152-5161). The fact that PACAP controls thymocyte proliferation suggests that this peptide is an important regulator of the maturation of immune cells (Delgado. (1996) Blood 87: 5152-5161).

This peptide has an indirect effect over lymphocytes maturation through the stimulation of interleukin 6 (IL-6) releases by follicular cells in pituitary. The IL-6 stimulates growth and differentiation of B cells and promotes the synthesis and secretion of immunoglobulins by these cells (Tatsuno et al. (1991) Endocrinology 129: 1797-1804; Yada et al. (1993) Peptides 14: 235-239). Additionally, PACAP activates and suppress the inflammatory response through the regulation of IL-6 and IL-10 (Martínez et al. (1996) J Immunol 156(11):4128-36; Martínez et al. (1998) J Neuroimmunol 85(2):155-67; Martínez et al. (1998) J Leukoc Biol 63(5):591-601). In activated macrophages, PACAP inhibit pro-inflammatory cytokines and stimulates the anti-inflammatory cytokines production, allowing the homeostasis of immune system. Besides, PACAP reduces the expression of co-stimulatory molecules B7.1/137.2 and subsequent activation of T helper cells (Th). On the other hand, PACAP inhibit the production of IL-6 through its receptor PAC-1 in activated macrophages, suppressing inflammation (Martínez et al. (1998) J Neuroimmunol 85(2):155-67; Martínez et al. (1998) J Leukoc Biol. 1998 May; 63(5):591-601). The inhibitory action of PACAP over IL-6 transcription in response to intense inflammatory stimuli or to intoxication helps tissue protection and immune system homeostasis (Martínez et al. (1998) J Neuroimmunol 85(2):155-67; Martinez et al. (1998) J Leukoc Biol. 63(5):591-601). In contrast, PACAP induce the expression of B7.2 and promotes cellular differentiation to Th2 in non-stimulated macrophages (Delgado y Ganea (2001) Arch Immunol Ther Exp (Warsz) 49(2):10110).

In general, the function of PACAP in modulation of mammal's immune system has been only partially elucidated in recent years. These studies demonstrated that PACAP regulates both, innate and adaptive immune system and modulates pro and anti-inflammatory response. Nevertheless, the existing information about the effect of this peptide on antiviral response is scarce. Recently, it was demonstrated in hepatitis B chronic patients, an increase in plasma PACAP-38 levels once the viremia was eliminated as a consequence of lamivudine treatment (Elefsiniotis et al. (2003) European Journal of Gastroenterology and Hepatology 15: 1209-1216). This finding suggests an effect over T cells immune response which results in a biochemical and histological disease remission in the patient's liver.

In fish, the in vivo studies about PACAP biological function published until now are mainly related with reproduction (Canosa et al. (2008) American Journal of Physiology (Regul Integr Comp Physiol) 295:1815-21), brain development (Sherwood et al. (2007) Peptides 28:1680-7) and appetite (Matsuda et al. (2005) Peptides 26:1611-6; Maruyama et al. (2006) Peptides 27:1820-6). Recently, it was demonstrated the biological function of this neuropeptide in growth and development of different larval teleost species (Lugo et al. (2008) Journal of Endocrinology 197: 583-97).

The knowledge about the function of PACAP in the modulation of fish immune response is limited to studies performed by the inventors' research group. It was demonstrated that recombinant Clarias gariepinus PACAP administration by baths or injection not only promotes growth but stimulates also innate immune parameters (lysozyme, nitric oxide derived metabolites and antioxidant defences) and acquired immunity (IgM) in larvae and juveniles treated (Carpio et al. (2008) Fish and Shellfish Immunology 25:439-45; Lugo et al. (2010) Fish and Shellfish Immunology 29:513520). These new properties were described in the patent application "Neuropéptidos para el cultivo de organismos acuáticos" (WO2007/059714).

In vertebrates, one of the first defense line against viral infections is the type I interferon (IFN) system. This system is activated by viral induction of type I interferons (IFN$\alpha$ and IFN$\beta$) through the IFN-$\alpha/\beta$ receptor which triggers signal transduction mediated by JAK-STAT. The induced cytokines produce a cell antiviral state producing the expression of proteins with antiviral activity such as 2',5' oligoadenilate synthetase, quinase R and the GTPases Mx (Goodbourn et al. (2000) Journal of General Virology 81: 2341-2364). Recent evidences establish that fish have an IFN system similar to mammals (Robertsen (2006) Fish and Shellfish Immunology 20: 172-191; Robertsen (2008) Fish and Shellfish Immunology 25: 351357). The interferons have been cloned in several fish species like zebrafish (Danio rerio), American catfish (Ictalurus punctatus) and Atlantic salmon (Salmo salar) (Altmann et al. (2003) Journal of Virology 77: 1992-2002; Lutfalla et al. (2003) BMC Genomics 4: 29; Robertsen et al. (2003) Journal of Interferon and Citokine Research 23: 601-612; Long et al. (2006) Fish and Shellfish Immunology 21: 42-59). Additionally, it has been identified several IFN regulatory factors, molecules of the JAK-STAT signaling pathway, Mx proteins and other genes stimulated by IFN in different fish species. It was reported antiviral activity mediated by Mx proteins in Salmo salar and Paralichtys olivaceus (reviewed by Robertsen (2006) Fish and Shellfish Immunology 20: 172-191).

Despite the fact that it has not been discovered IFN like genes in crustaceans yet, it has been observed a negative regulation of STAT molecules (these are molecules which are activated in the IFN response in vertebrates) in response of WSSV infection. The negative regulation of STAT during a viral infection antagonizes the type I IFN response in mammals (reviewed by Johnson et al. (2008) Vaccine 26: 4885-4992). In bivalves, the knowledge of antiviral response is even less. There are evidences of antiviral activity in the hemolymph of these organisms and it has been suggested the presence of an IFN like mechanism (Olicarda et al. (2005) Antiviral Research 66(2-3): 147-152; Defer et al., (2009) Aquaculture 293(1-2): 1-7).

In aquaculture, it is of great interest the development of new compounds or compositions that can be employed in the control of viral infections, due to the damages that they cause in this activity.

experimentally in vivo infected with VHSV (100 μL of 1×10⁷ TCID50/mL per fish). Five pools of total RNA from spleen of 5 fish were sampled at random at 3, 7 and 10 days after viral infection. The expression levels were analyzed by qPCR in triplicate. Data are expressed as mean of relative expression of VPAC-1 related to the endogenous elongation factor EF1α±standard deviation (SD). * (p<0.05).

Figure 6:
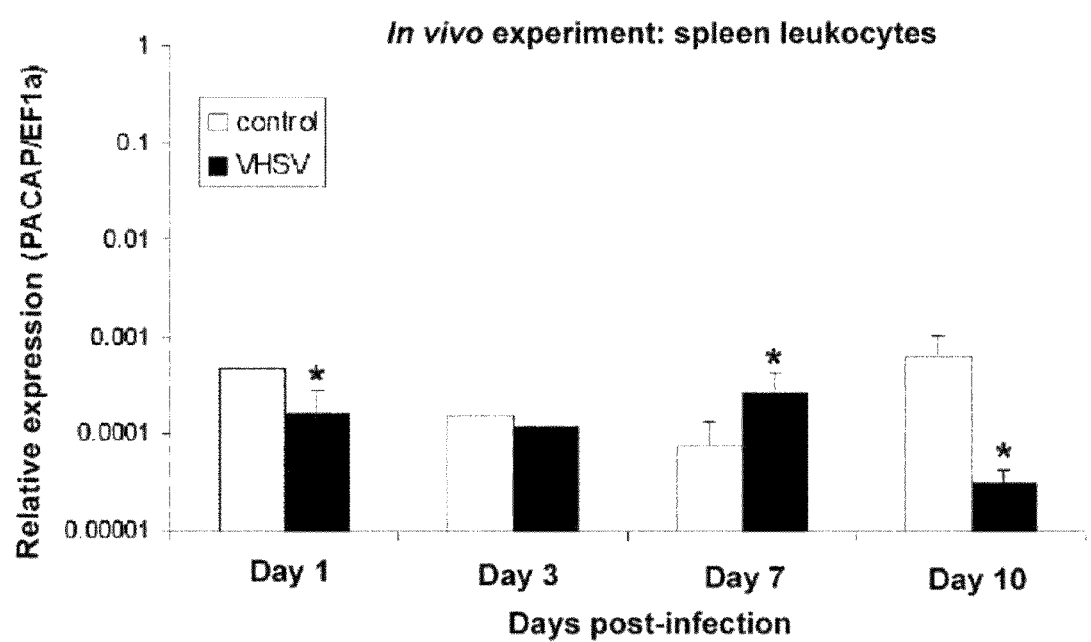

FIG. 6. Expression analysis by real time PCR of PACAP in spleen leukocytes from rainbow trout (*O. mykiss*) experimentally in vivo infected with VHSV (100 μL of 1×10⁷ TCID50/mL per fish). Five pools of total RNA from spleen of 5 fish were sampled at random at 3, 7 and 10 days after viral infection. The expression levels were analyzed by qPCR in triplicate. Data are expressed as mean of relative expression of PACAP related to the endogenous elongation factor EF1α±standard deviation (SD). * (p<0.05).

Figure 7A:
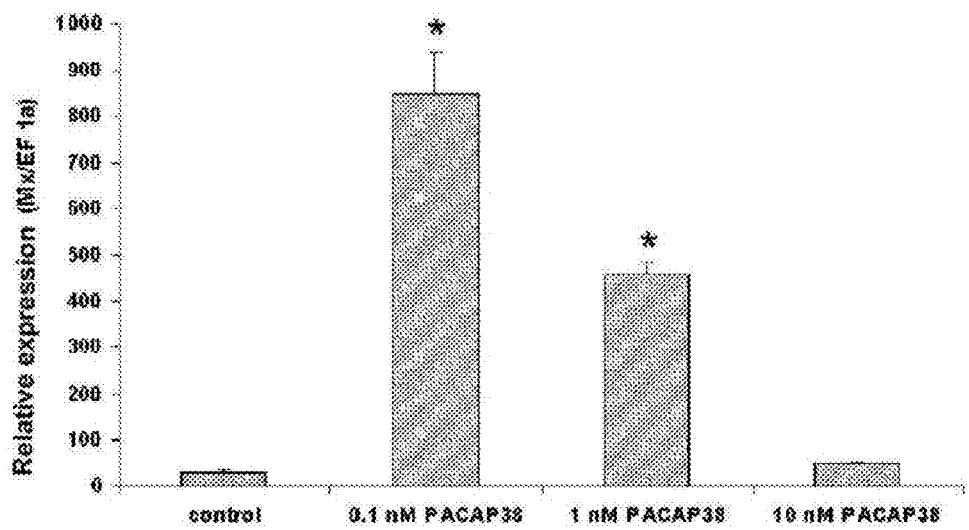

FIG. 7A. Expression analysis by real time PCR of the in vitro effect of PACAP38 over the transcription of Mx protein coding gene in peripheral blood leukocytes of healthy rainbow trout. The effects of PACAP administration at a concentration of $10^{-10}$, $10^{-9}$ and $10^{-8}$ M was evaluated at 48 h post-treatment. The experiment was repeated 4 times. The leukocytes culture was treated by duplicated and the qPCR was performed by triplicate. Data are expressed as mean of relative expression of Mx related to the endogenous elongation factor EF1α±standard deviation (SD). * (p<0.05).

Figure 7B:
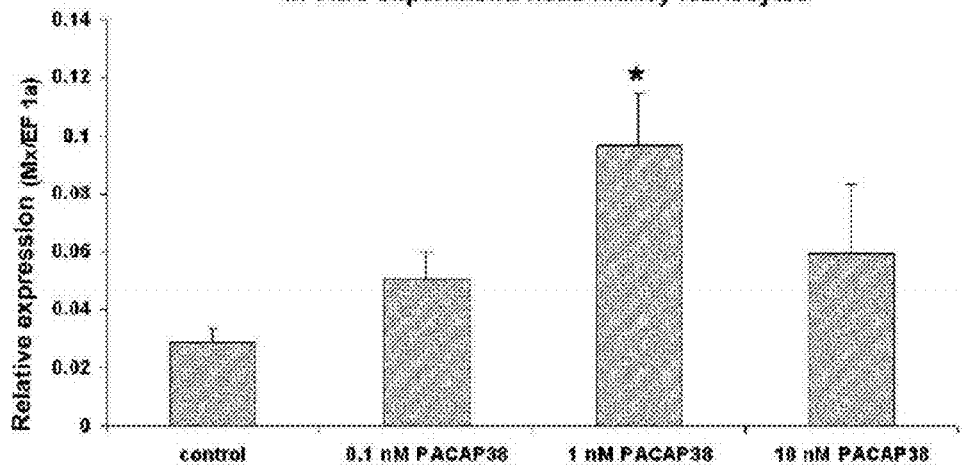

FIG. 7B. Expression analysis by real time PCR of the in vitro effect of PACAP38 over the transcription of Mx protein coding gene in head kidney of healthy rainbow trout. The effects of PACAP administration at a concentration of $10^{-10}$, $10^{-9}$ and $10^{-8}$ M was evaluated at 48 h post-treatment. The experiment was repeated 4 times. The leukocytes culture was treated by duplicated and the qPCR was performed by triplicate. Data are expressed as mean of relative expression of Mx related to the endogenous elongation factor EF1α±standard deviation (SD). * (p<0.05).

Figure 8A:
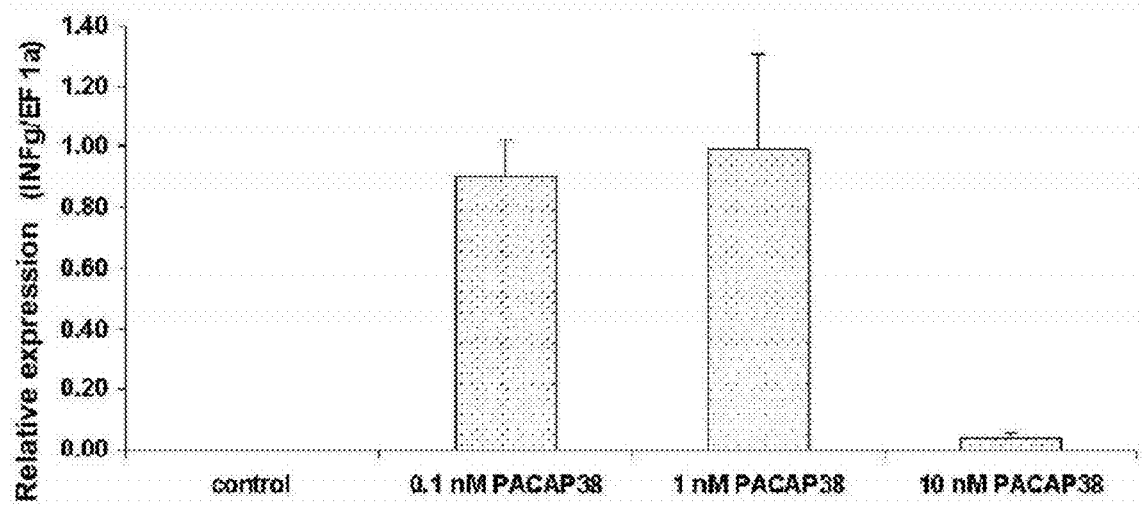

FIG. 8A. Expression analysis by real time PCR of the in vitro effect of PACAP38 over the transcription of IFN γ coding gene in peripheral blood leukocytes of healthy rainbow trout. The effects of PACAP administration at a concentration of $10^{-10}$, $10^{-9}$ and $10^{-8}$ M was evaluated at 48 h post-treatment. The experiment was repeated 4 times. The leukocytes culture was treated by duplicated and the qPCR was performed by triplicate. Data are expressed as mean of relative expression of IFN γ related to the endogenous elongation factor EF1α±standard deviation (SD). * (p<0.05).

Figure 8B:
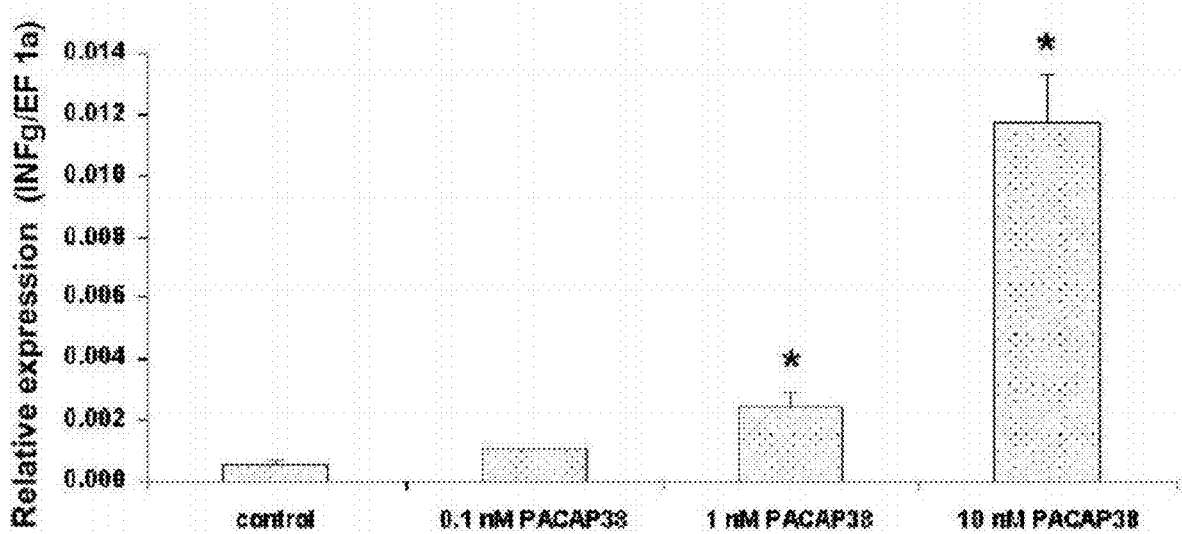

FIG. 8B. Expression analysis by real time PCR of the in vitro effect of PACAP38 over the transcription of IFN γ coding gene of healthy rainbow trout. The effects of PACAP administration at a concentration of $10^{-10}$, $10^{-9}$ and $10^{-8}$ M was evaluated at 48 h post-treatment. The experiment was repeated 4 times. The leukocytes culture was treated by duplicated and the qPCR was performed by triplicate. Data are expressed as mean of relative expression of IFN γ related to the endogenous elongation factor EF1α±standard deviation (SD). * (p<0.05).

Figure 9A:
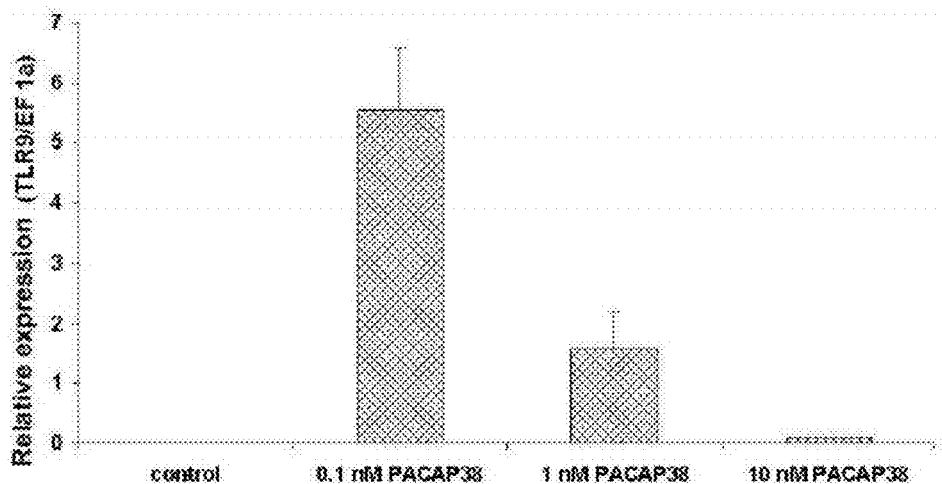

FIG. 9A. Expression analysis by real time PCR of the in vitro effect of PACAP38 over the transcription of TLR9 coding gene in peripheral blood leukocytes of healthy rainbow trout. The effects of PACAP administration at a concentration of $10^{-10}$, $10^{-9}$ and $10^{-8}$ M was evaluated at 48 h post-treatment. The experiment was repeated 4 times. The leukocytes culture was treated by duplicated and the qPCR was performed by triplicate. Data are expressed as mean of relative expression of TLR9 related to the endogenous elongation factor EF1α±standard deviation (SD). * (p<0.05).

Figure 9B:
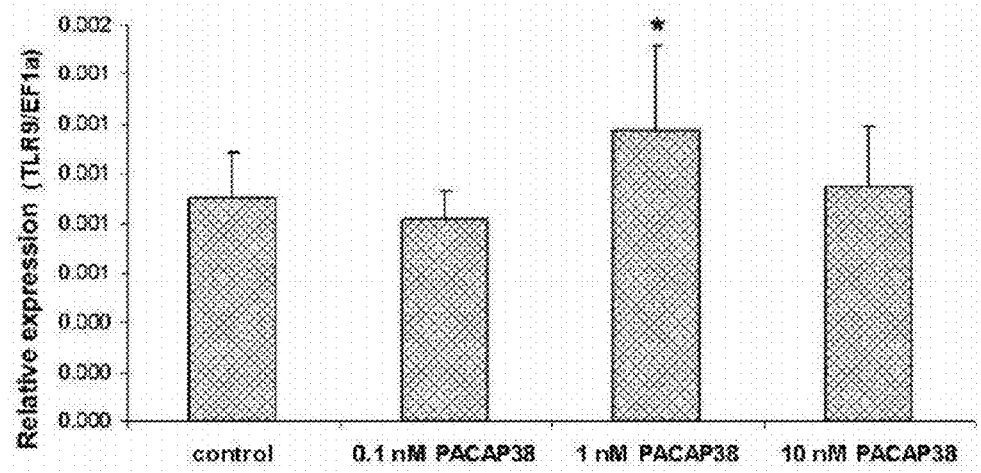

FIG. 9B. Expression analysis by real time PCR of the in vitro effect of PACAP38 over the transcription of TLR9 coding gene in head kidney of healthy rainbow trout. The effects of PACAP administration at a concentration of $10^{-10}$, $10^{-9}$ and $10^{-8}$ M was evaluated at 48 h post-treatment. The experiment was repeated 4 times. The leukocytes culture was treated by duplicated and the qPCR was performed by triplicate. Data are expressed as mean of relative expression of TLR9 related to the endogenous elongation factor EF1α±standard deviation (SD). * (p<0.05).

Figure 10:
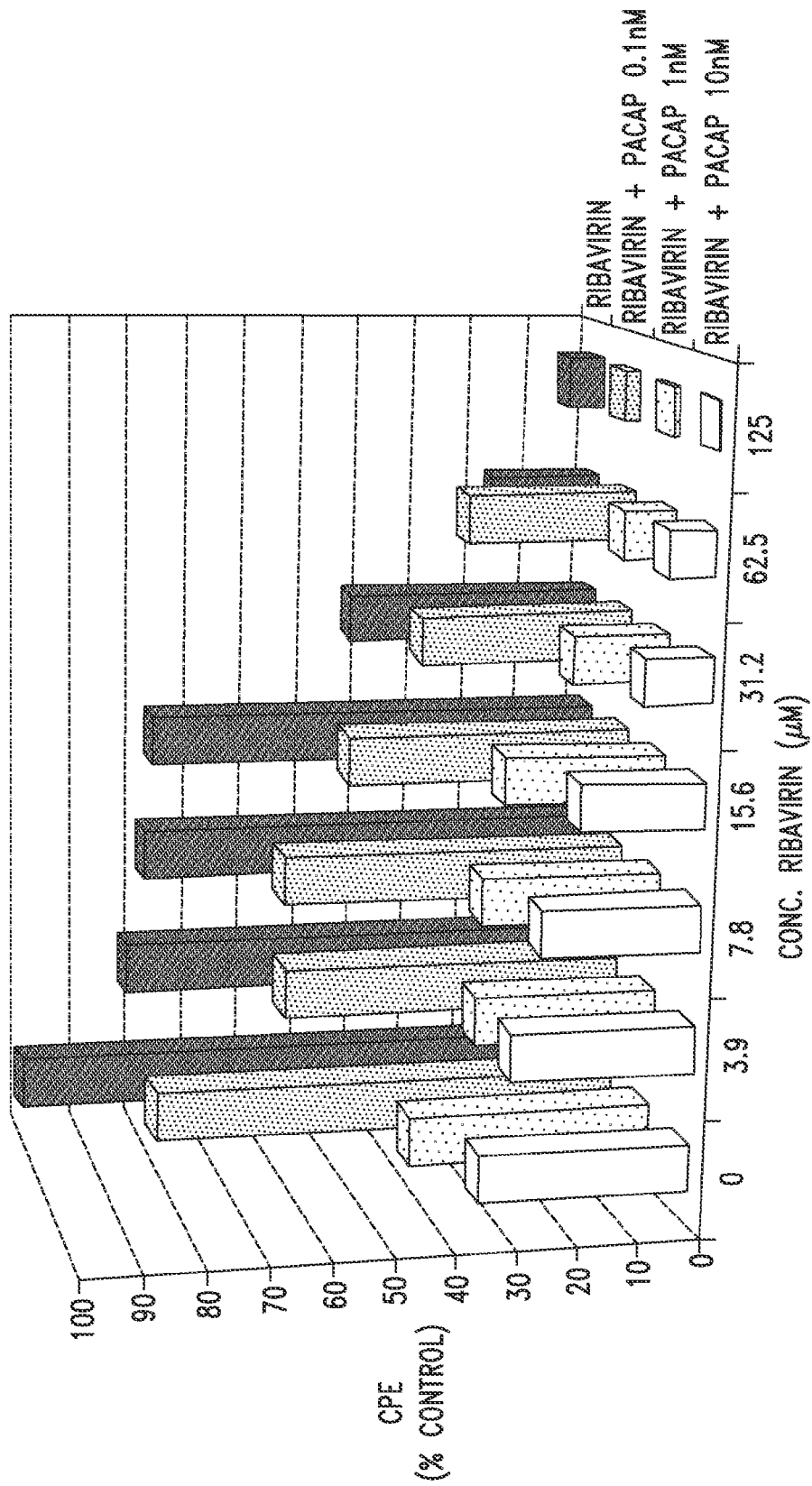

FIG. 10. In vitro assays to determine the antiviral activity of PACAP-ribavirin combinations (Rib-PACAP). At 24 h previous to virus infection, cells were treated with the "antiviral" or the combinations PACAP-antivirals. Positive control (c+): Cells infected with virus without antiviral treatment. Negative control (c−): Cells non-infected and non-treated. Cells were infected with virus during 30 min to allow adsorption. Afterward, they were washed with PBS and the different treatments were added. The inhibition of cytopathic effects (CPE) was evaluated employing the crystal violet stain (absorbance at 550 nm).

DESCRIPTION OF THE INVENTION

The present invention provides a solution to the above described problem providing a new alternative to control viral infections in aquaculture, by the use of PACAP in the manufacture of compositions for the treatment of viral infections and infectious diseases caused by virus in aquatic organisms.

The term "treatment" in the context of the present invention is related to any beneficial effect in disease remission which includes attenuation, reduction or decrease of the pathological development after the disease onset.

The term "antiviral", as it is used in the present invention, includes any molecule defined as antiviral in the previous art or its analogs, functional derivatives or active fragments.

The term "Pituitary Adenylate cyclase Activating Polypeptide (PACAP)", as it is used in the present invention, includes this molecule in any variant (PACAP27 or PACAP38), either isolated from its natural source, or synthetic, or produced by recombinant DNA technology.

In one embodiment of the invention, variants of the neuropeptide PACAP are administered alone or in combination with a known antiviral molecule to fish, crustaceans and bivalves, by immersion baths with 2-3 days intervals. As a feed additive, PACAP is also administrated alone or in combination with a known antiviral molecule.

In the present invention, it was demonstrated that PACAP containing compositions administered by immersion baths, injection or orally were effective increasing survival of the aquatic organism infected by virus and treated with them. No decrease in the weight of treated fish was observed. In some cases an overall weight increase was obtained in infected and treated animals as compared to infected and non-treated. The analysis of tissue samples and susceptible organs by RT-PCR showed a decreased in the viral load in the animals infected and treated.

Up to this invention there was no knowledge about whether or not PACAP modulated the antiviral response in fish, crustaceans and bivalves and the mechanisms involved. The present invention demonstrates, for the first time, both in vitro and in vivo, a relationship between PACAP and the response to virus in fish, crustaceans and bivalves. Additionally, described for the first time is an unexpected positive effect on PACAP molecules involved in antiviral response, such as Mx protein, interferon gamma (IFN γ) and toll like receptor 9 (TLR9) as well as a differential regulation of this peptide and its receptors in cells of the immune system of fish treated with virus and/or poly I:C, both in vitro and in vivo.

The treatment of viral infections in fish, crustaceans and bivalves by the administration of PACAP or a combination of PACAP with a molecule with known antiviral action in fish has not been revealed or suggested previously in the state of the art.

In the context of the present invention, administration of PACAP and the antiviral molecule may be simultaneous (in a single formulation), sequential or separate over time. The preparations are administered to aquatic organisms by oral route, injection or immersion baths.

In the present invention, fish, crustaceans and bivalves are treated with PACAP and preparations containing antiviral molecules combined with PACAP. Unexpectedly, it was observed that the neuropeptide PACAP has antiviral activity in fish, crustaceans and bivalves. On the other hand, it was shown that the combination of PACAP with substances with known antiviral activity produce a higher antiviral response (synergistic effect) as compared to the PACAP alone, both in vitro and in vivo. In fish, so far, no biological functions have been assigned to PACAP in the antiviral response. Moreover, to date neither PACAP nor another peptide belonging to the superfamily of secretin and glucagon has been isolated in shrimp or shellfish. The present knowledge of this peptide in these taxonomic groups is only based on experimental evidence of growth stimulation in shrimps by exogenous administration of recombinant fish PACAP (patent application publication number WO2007/059714 international). Therefore, until the present invention, no knowledge about its possible relationship with response to virus in crustaceans and bivalves existed.

Another object of this invention is a composition for the treatment of viral and infectious diseases caused by viruses in aquatic organisms which comprises the "activating polypeptide pituitary adenylate cyclase" (PACAP). In one embodiment of the invention, the PACAP, as part of the composition, is obtained by isolation either from its natural source, synthetically or by recombinant DNA technology. It is administered either orally, by injection or immersion baths. In one embodiment of the invention PACAP is a polypeptide sequence isolated from fish.

The present invention also relates to a veterinary combination which comprises "activating polypeptide pituitary adenylate cyclase" (PACAP) and an antiviral molecule. In one embodiment of the invention the antiviral molecule is ribavirin or a ribavirin analog. The elements that are part of the combination, the antiviral molecule and PACAP, are administered simultaneously, separately or sequentially during the same treatment. In one embodiment of the invention, the combination is used in the treatment of viral and infectious diseases caused by viruses in aquatic organisms. In these, the PACAP and antiviral are administered orally, by injection or immersion baths.

In one embodiment of the invention, PACAP is applied as formulated feed at a concentration of 50-750 mg/kg of feed and the antiviral molecule at a concentration of 100 to 2000 mg/kg of feed. In a second embodiment of the invention, the PACAP is applied to fish by injection at a concentration of 0.1-10 μg per gram of body weight and the antiviral at a concentration of 1-50 μg/g, as part of the veterinary combination. In another embodiment of the invention in this combination, the PACAP is applied to fish or crustaceans by immersion baths at a concentration of 50-1000 μg per liter of water and the concentration of the antiviral is 100-2000 μg/L.

In the invention, both the PACAP when used as an antiviral, or in combination with a known antiviral molecule is applied to a variety of aquatic organisms. For example, they include salmonids, penaeid shrimps, and bivalves.

The composition comprising PACAP and the combination with an antiviral molecule are useful in therapeutic treatment of viral infections caused by viruses of the Herpesviridae, Papovaviridae, Togaviridae, Retroviridae, Reoviridae, Birnaviridae and Picornaviridae families.

In the invention, both the PACAP when used as an antiviral and the combination with an antiviral molecule, are used to control infections caused by IPNV, VHSV and ISAV. Also, they are used in the therapeutic treatment of viral infections caused by WSSV, YHV, TSV, IHNNV and MBV.

It is also part of the present invention a method for the control of viral infections in aquaculture management comprising the administration of PACAP or veterinary combinations comprising PACAP to aquatic organisms in culture.

EXAMPLES

Example 1

PAC-1 Receptor Expression in Leukocytes from Head Kidney of Rainbow Trout (*O. mykiss*) Cells Treated with Poly I:C and IPNV and in the Macrophage Cell Line of Rainbow Trout (*O. mykiss*) RTS-11 Infected with VHSV In Vitro Juvenile rainbow trout (*O. mykiss*) was used from 9 to 12 grams and 7 months of age, VHSV and IPNV free. Fish were maintained at 14° C. with water circulation. Food was administered twice a day ad libitum. The virus, VHSV (strain 0771) and IPNV (strain Sp) were propagated in the rainbow trout gonad cell line RTG-2 (Sena and Rio (1975) Infect Immun 11:815-22). Cells were grown in minimal essential medium (MEM, Invitrogen, USA) supplemented with 10% of fetal calf serum (FCS, Invitrogen) containing 100 IU/mL of penicillin and 100 μg/mL of streptomycin. The viruses were inoculated into RTG-2 cells grown in MEM with antibiotics and 2% FCS at 14° C. When extensive cytopathic effects were observed, the culture supernatants were harvested and centrifuged to remove cellular debris. For the experiments, the clarified culture supernatants were used. The viral titers were determined in 96-well plates as reported by Reed and Muench (Reed and Muench (1998) J Hyg 27:280-9).

Head kidney leukocytes were isolated from 4 trout following the method described by Graham and Secombes (Graham and Secombe (1998) Immunology 65:293-7). Briefly, anterior kidney was removed aseptically and passed through a nylon mesh of 100μ using medium Leibovitz (L-15, Gibco, UK) supplemented with penicillin 100 IU/mL, streptomycin (100 mg/mL), heparin (10 units/mL) and 2% FCS. The resulting cell suspension was carefully placed on a Percoll gradient to 51%. The ring of cells corresponding to leukocytes was removed carefully, washed twice in FCS containing L-15 at 0.1%. The cells were resuspended in L-15 with 5% FCS at a concentration of $5\times10^6$ cells per ml and dispensed in 24-well plates at 1 mL per well. The infected leukocytes were exposed to 30 μg/mL de poly I:C (Sigma) or infected with IPNV at a MOI of 0.1 and incubated at 14° C. during 4 hours, 24 hours and 48 hours periods.

Finally, total RNA was purified from leukocytes cultures using the method described by Chomczynski and Sacchi (Chomczynski and Sacchi (1987) Anal. Biochem. 162:156-9) to evaluate the expression levels of the PAC-1 receptor on leukocytes untreated and treated with Poly I:C or infected with viruses. Samples were treated with the RQ1 RNase-free DNase (Promega), in order to remove genomic DNA present in the samples. For the synthesis of complementary DNA (cDNA) was used a commercial reagent SuperScript III (Invitrogen) based on the reverse transcriptase. For quantitative PCR reactions (qPCR) was used a mixture of PCR from commercial sources: Power SYBR Green PCR Master Mix (Applied Biosystems). The qPCR results were normalized against a constitutive endogenous gene expression, specifically elongation factor 1α (EF 1α) and were performed in triplicate. The results were expressed as $2^{-\Delta Ct}$, where ΔCt is equal to the remainder of the gene Ct value minus the assessed value of Ct normalizer gene (EF 1α).

Figure 1:
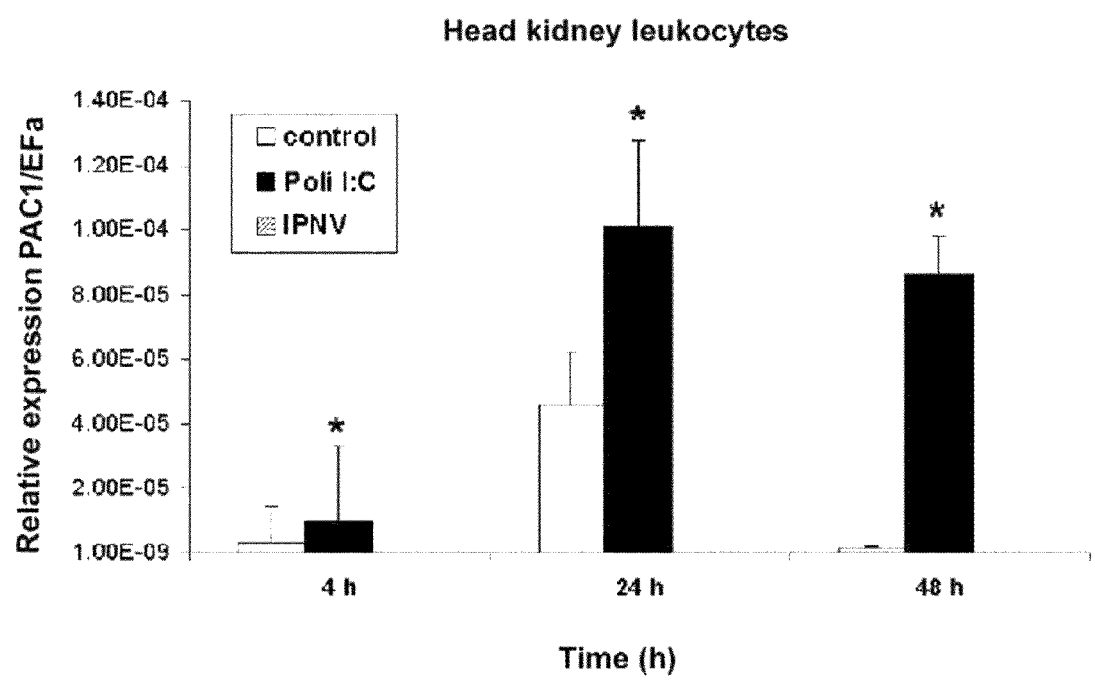
FIG. 1. Expression analysis by real time PCR of PAC-1 receptor in head kidney leukocytes from rainbow trout (Oncorhynchus mykiss) treated with poly I:C (30 µg/mL) or infected with IPNV (multiplicity of infection (m.o.i) of 0.1) at 4, 24 and 48 h from the beginning of the experiment. The leukocytes cultures were treated by duplicated and the expression levels were analyzed by qPCR in triplicate. Data are expressed as mean of relative expression of PAC-1 related to the endogenous elongation factor EF1$\alpha$±standard deviation (SD). * ($p<0.05$).

The result was that levels of PAC-1 was over-expressed in cultured leukocytes treated with poly I:C at 4, 24 and 48 hours of the experiment, suggesting that PAC-1 receptor is involved in the response to virus in fish, taking into account that poly I:C is a molecule that is structurally the same as double-stranded RNA, an effect similar to a viral infection (many viruses have RNA genomes). These results are shown in FIG. 1. Poly I:C interacts with toll-like receptor-3 (TLR3) that is expressed in intracellular compartments of B cells and dendritic cells. The TLR-3 is stimulated by viruses in nature.

Moreover, the expression levels of PAC-1 became detectable values of leukocytes in untreated cultures to undetectable levels in cultures of leukocytes infected with IPNV at 4, 24 and 48 hours after infection, confirming involvement of this receptor that specifically binds to PACAP in the antiviral response in fish (FIG. 1). The differences observed between the effects of viral mimetic poly I:C and that of IPNV could be associated with a specific effect of the virus in infected cells, probably to their advantage.

Figure 2:
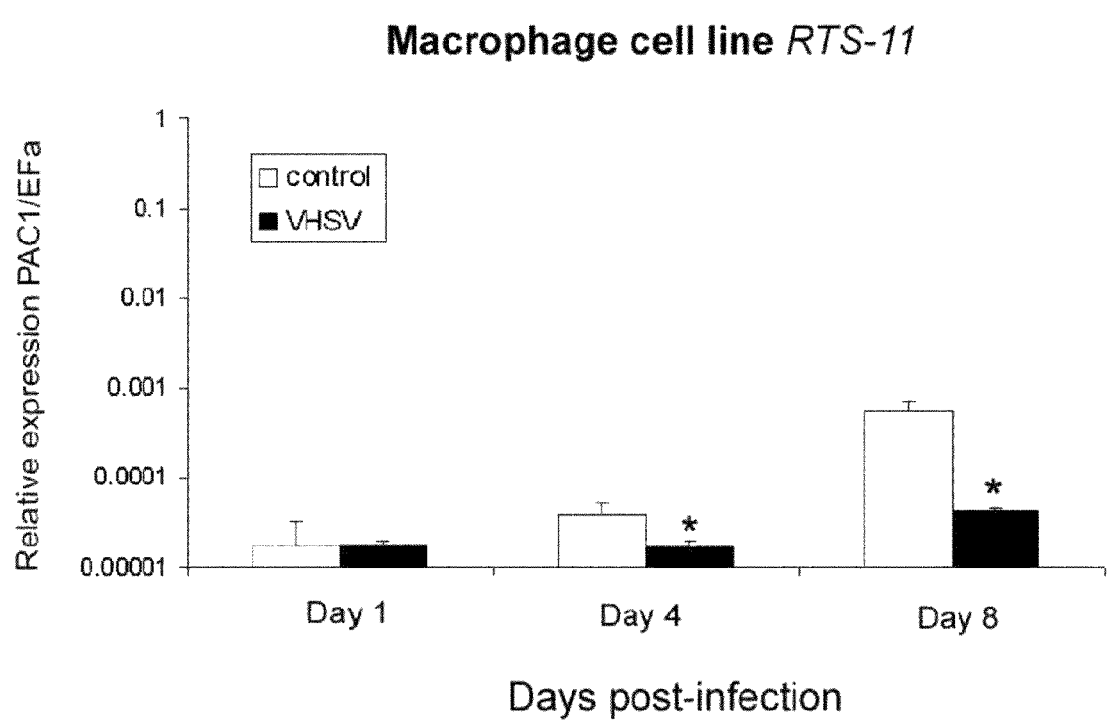
FIG. 2. Expression analysis by real time PCR of PAC-1 receptor in the macrophage cell line from O. mykiss RTS-11 infected in vitro with VHSV (m.o.i of 0.1) at 1, 4 and 8 h from the beginning of the experiment. The experiment was done in duplicated and the expression levels were analyzed by qPCR in triplicate. Data are expressed as mean of relative expression of PAC-1 related to the endogenous elongation factor EF1$\alpha$±standard deviation (SD). * ($p<0.05$).

Additionally, the expression levels of PAC-1 were evaluated in the macrophage cell line trout (*O. mykiss*) RTS-11 infected with VHSV, the process of viral infection of the line RTS-11 was similar to that described above for the RTG-2 line. Similarly, a down regulation of the expression levels of PAC-1 to 4 and 8 was observed days after infection with VHSV (FIG. 2).

Example 2

Expression of VPAC-1 Receptor in Leukocytes from Anterior Kidney of Rainbow Trout (*Oncorhynchus mykiss*) Cells Treated with Poly I:C and VHSV To assess the levels of expression of VPAC-1 receptor an experimental design similar to the one described in Example 1 was performed.

Figure 3:
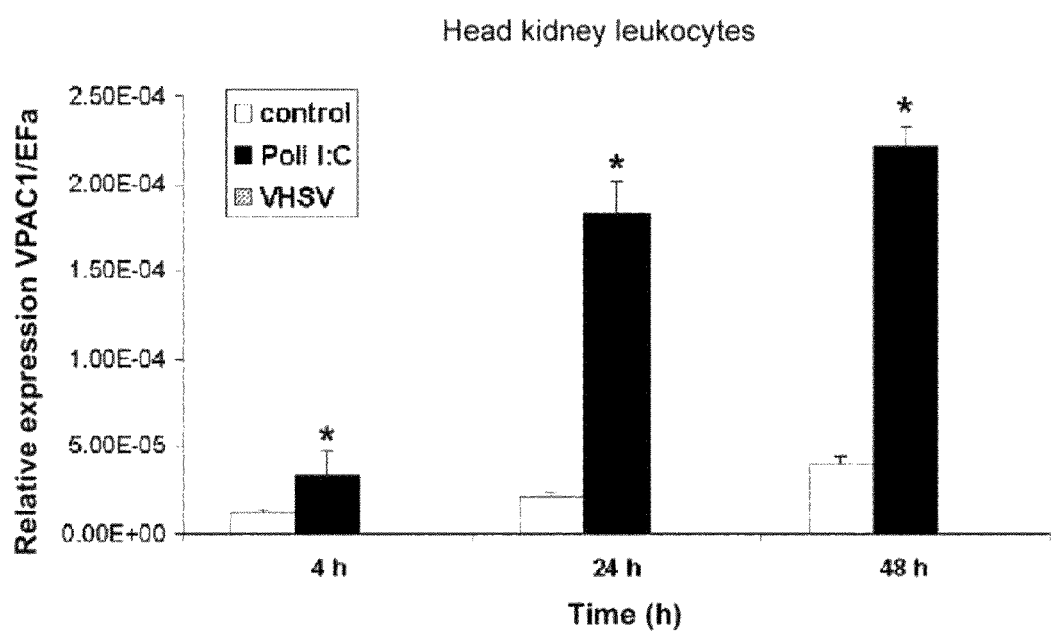
FIG. 3. Expression analysis by real time PCR of VPAC-1 receptor in head kidney leukocytes from rainbow trout (O. mykiss) treated with poly I:C (30 µg/mL) or infected with VHSV (multiplicity of infection, m.o.i of 0.1) at 4, 24 and 48 h from the beginning of the experiment. The leukocytes cultures were treated by duplicated and the expression levels were analyzed by qPCR in triplicate. Data are expressed as mean of relative expression of VPAC-1 related to the endogenous elongation factor EF1$\alpha$±standard deviation (SD). * ($p<0.05$).

The result was that the levels of VPAC-1 is over-expressed in cultured leukocytes treated with poly I:C at 4, 24 and 48 hours of the experiment, suggesting that VPAC-1 receptor as the PAC-1 is involved in the response to virus in fish, taking into account that poly I:C is considered a viral mimetic molecule (FIG. 3).

Moreover, the expression levels of VPAC-1 were undetectable in cultures of leukocytes infected with VHSV at 4, 24 and 48 hours after infection, confirming an involvement of this receptor that binds PACAP and VIP with the same affinity in the antiviral response in fish (FIG. 3).

As observed with PAC-1 receptor in cultured anterior kidney leukocytes infected with IPNV, the observed differences in the regulation of VPAC-1 by treatment of leukocytes in vitro with poly I:C and the infection VHSV could be associated with a specific effect of the virus as a biological entity complete in infected cells, probably to their advantage.

Example 3

Expression of PACAP and PAC-1 Receptors and VPAC-1 in Leukocytes from Spleen and Anterior Kidney of Rainbow Trout (*Oncorhynchus mykiss*) Infected with VHSV In Vivo VHSV (strain 0771) was propagated in the cell line RTG-2 (Sena and Rio (1975) Infect Immun 11:815-22). In summary, the viruses were inoculated in RTG-2 cell line grown in MEM with antibiotics (100 IU/mL penicillin and 100 μg/mL streptomycin) and 2% FCS at 14 C. When extensive cytopathic effects were observed, the culture supernatants were harvested and centrifuged to remove cellular debris. For infection of trout were used clarified culture supernatants. The viral titers were determined in 96-well plates as reported by Reed and Muench (Reed and Muench (1998) J Hyg 27:280-9).

Juvenile rainbow trout (*O. mykiss*) was used from 9 to 12 grams and 7 months old and VHSV and IPNV free. Fish were maintained at 14 C with water circulation. Food was administered twice a day ad libitum. Two experimental groups were formed of 20 trout each group, one group was injected with virus solution (100 L of $1\times10^7$ TCID50/mL per fish) and the other group (used as negative control) was injected with culture medium RTG-2 not infected with VHSV.

At days 1, 3, 7 and 10 post-injection, 5 trout were taken at random and were sacrificed by over-exposure to the anesthetic MS-22. Subsequently the kidney was removed and spleen above to proceed with the purification of total RNA from these organs, according to the method described by Chomczynski and Sacchi (Chomczynski and Sacchi (1987) Anal. Biochem. 162:156-9). CDNA synthesis and reactions of quantitative PCR performed as described in Example 1.

For the reactions of reverse transcription (RT), five total RNAs from five individuals from each experimental group selected at random on day 1, 3, 7 and 10 of the experiment were pooled.

Figure 4A:
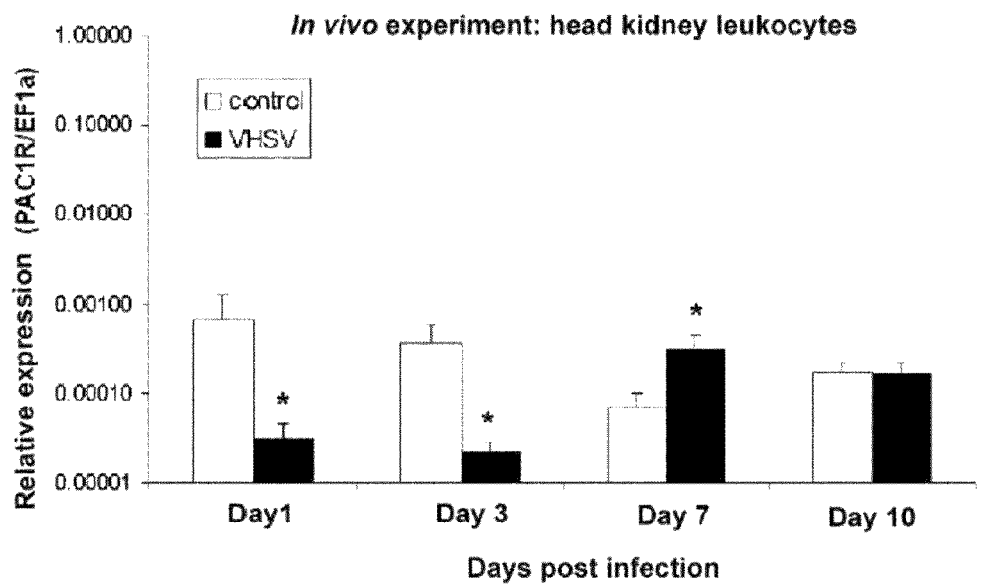
FIG. 4A. Expression analysis by real time PCR of PAC-1 receptor in head kidney leukocytes from rainbow trout (O. mykiss) experimentally in vivo infected with VHSV (100 µL of $1\times10^7$ TCID50 (viral titer in culture supernatant/mL per fish). Five pools of total RNA from head kidney of 5 fish were sampled at random at 3, 7 and 10 days after viral infection. The expression levels were analyzed by qPCR in triplicate. Data are expressed as mean of relative expression of PAC-1 related to the endogenous elongation factor EF1$\alpha$±standard deviation (SD). * ($p<0.05$).
Figure 4B:
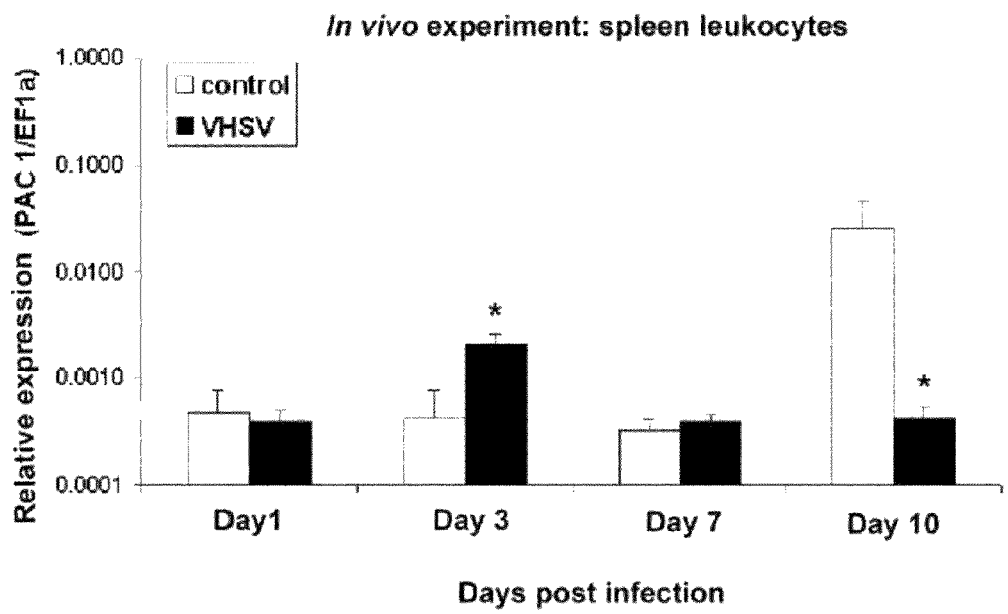
FIG. 4B. Expression analysis by real time PCR of PAC-1 receptor in spleen from rainbow trout (O. mykiss) experimentally in vivo infected with VHSV (100 µL of $1\times10^7$ TCID50 (viral titer in culture supernatant/mL per fish). Five pools of total RNA from spleen of 5 fish were sampled at random at 3, 7 and 10 days after viral infection. The expression levels were analyzed by qPCR in triplicate. Data are expressed as mean of relative expression of PAC-1 related to the endogenous elongation factor EF1$\alpha$±standard deviation (SD). * ($p<0.05$).
Figure 5A:
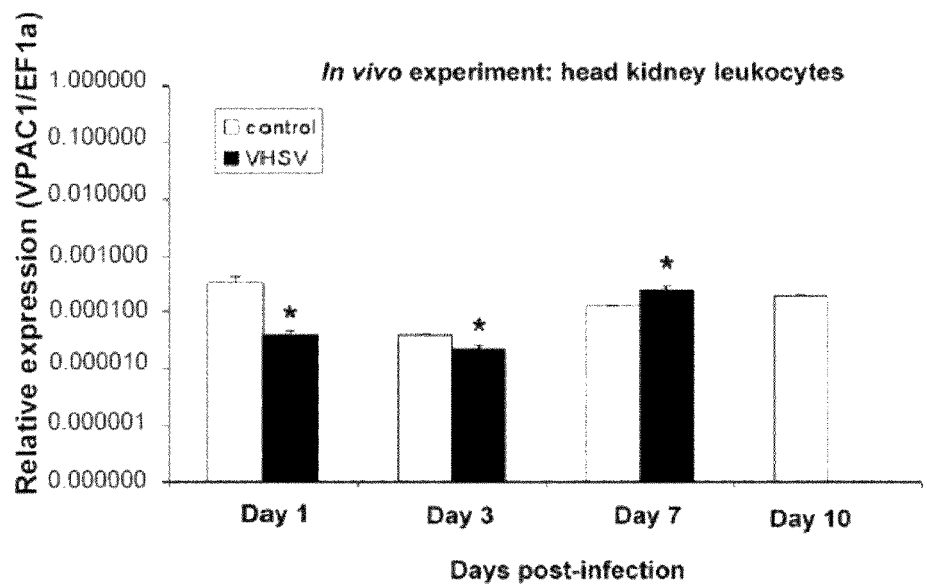
FIG. 5A. Expression analysis by real time PCR of VPAC-1 receptor in head kidney leukocytes from rainbow trout (O. mykiss) experimentally in vivo infected with VHSV (100 µL of $1\times10^7$ TCID50/mL per fish). Five pools of total RNA from head kidney of 5 fish were sampled at random at 3, 7 and 10 days after viral infection. The expression levels were analyzed by qPCR in triplicate. Data are expressed as mean of relative expression of VPAC-1 related to the endogenous elongation factor EF1$\alpha$±standard deviation (SD). * ($p<0.05$).
Figure 5B:
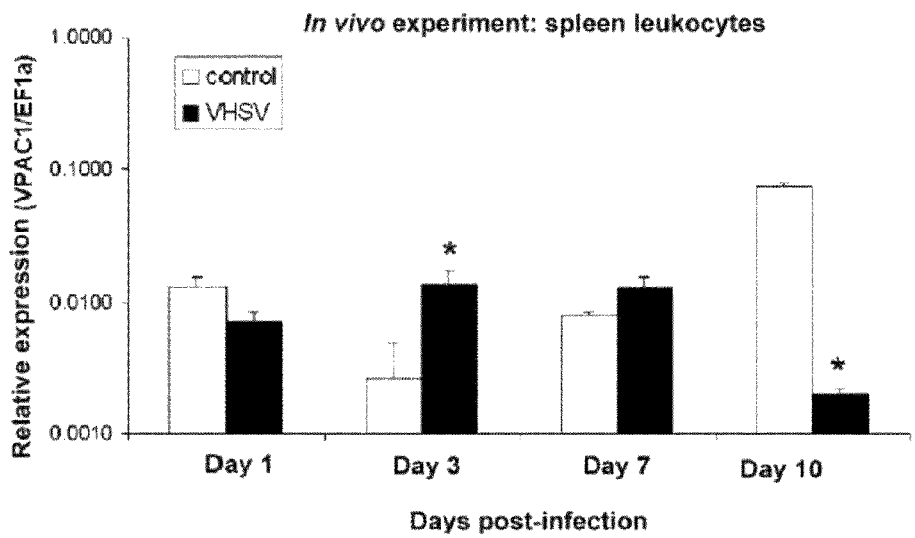
FIG. 5B. Expression analysis by real time PCR of VPAC-1 receptor in spleen from rainbow trout (O. mykiss)

The result was that in the spleen, PAC-1 and VPAC-1 receptors are over-expressed at day 3 post-injection compared to negative control. The expression levels are lower than the control group at day 10 post-injection. In anterior kidney, PAC-1 and VPAC-1 receptors have lower expression levels in the control group at day 1 and 3, where the values of VPAC-1 to day 10 undetectable. At day 7 both receptors increase their levels of expression compared to negative control group. It was also observed that both receptors have a similar expression pattern over time after viral infection (FIGS. 4 and 5).

The PACAP expression values at day 1 are lower compared to its negative control. On day 7 these expression values are superior. These results correlate with those of its two receptors VPAC-1 and PAC-1, in the sense that levels of receptor expression showed a tendency to be lower (day 1) and higher (day 7) compared to negative control group. At day 10 the expression of PACAP values are lower compared to negative control group (FIGS. 4, 5 and 6).

The variation in expression levels of PACAP and its receptors PAC-1 and VPAC-1 in the spleen and anterior kidney of fish experimentally infected with VHSV and IPNV demonstrate the involvement of both receptors in the antiviral response in fish in vivo. This was confirmed in challenge experiments in which a positive effect of PACAP was observed in the antiviral response in salmonids, increasing the survival of infected fish, enhancing the immune response to viral infection and clearing the virus from the organs and fluids capable to perform viral replication.

Example 4

PACAP Effect on Transcription of Proteins Mx, IFN and TLR9 in Peripheral Blood Leukocytes and Anterior Kidney of Healthy Rainbow Trout (*Oncorhynchus mykiss*)

Juvenile rainbow trout (*O. mykiss*) was used of approximately 50 grams, VHSV and IPNV free. Fish (n=5) were anesthetized with methanesulfonic acid salt (Sigma, USA) and were removed aseptically, first peripheral blood from the tail vein and then the anterior kidney were isolated from peripheral blood leukocytes from anterior kidney and trout from 5 independently, following the method described by Graham and Secombe (Graham and Secombe (1998) Immunology 65:293-7).

The peripheral blood of each fish was diluted 4 times in half Leibovitz (L-15, Gibco, UK) supplemented with penicillin 100 IU/mL, streptomycin (100 µg/mL), heparin (10 units/mL) and 2% FCS and placed carefully on a Percoll gradient to 51%. The ring of cells corresponding to leukocytes was removed carefully, washed twice in L-15 containing 0.1% FCS.

The anterior kidney was passed through a nylon mesh of 100 µm Leibovitz (L-15, Gibco, UK) supplemented with penicillin 100 IU/mL, streptomycin (100 µg/mL), heparin (10 units/mL) and 2% FCS. The resulting cell suspension was diluted 1:4 in the same medium supplemented L-15 and placed carefully on a Percoll gradient to 51%. The ring of cells corresponding to leukocytes was removed carefully, washed twice in L-15 containing 0.1% FCS.

The cells were suspended in L-15 with 5% FCS at a concentration of 5×106 cells per ml and dispensed in 24-well plates at 1 mL per well. The leukocytes were treated with 3 doses of PACAP38 from *Clarias gariepinus* obtained by chemical synthesis ($10^{-10}$ M, $10^{-9}$ M and $10^{-8}$ M) in duplicate and used as negative control untreated leukocytes dispensed in duplicate.

The levels of Mx, IFN and TLR9 were evaluated 48 hours after treatment. In order to do so, total RNA was purified from leukocyte cultures treated with PACAP by the method described by Chomczynski and Sacchi (Chomczynski and Sacchi (1987) Anal. Biochem. 162:156-9).

The primers designed to amplify Mx, IFN γ and TLR9 do not discriminate between cDNA and genomic DNA, total RNAs were treated purified from different tissues with a DNA nuclease, specifically with RQ1 RNase-free DNase (Promega) in order to remove genomic DNA may be present in the samples.

For the synthesis of cDNA it was used a commercial reagent kit uses SuperScript III reverse transcriptase (Invitrogen). Finally, for quantitative PCR reactions (qPCR) was used a mixture of PCR from commercial sources: Power SYBR Green PCR Master Mix (Applied Biosystems). The qPCR results were normalized against a constitutive endogenous constitutive expression gene specifically elongation 1α (EF 1α) and were performed in triplicate. The results were expressed as $2^{-\Delta Ct}$, where $\Delta Ct$ is equal to the remainder of the gene Ct value minus the assessed value of Ct normalizer gene EF 1α).

The Mx protein levels increase after 48 hours of treatment in cultures of peripheral blood leukocytes treated with $10^{-10}$ M PACAP38. A dose of $10^{-9}$ M, there is also a stimulatory effect of PACAP38 on the transcription of Mx proteins relative to negative control, but the expression levels detected were below levels obtained with the dose of $10^{-10}$ M. A dose of $10^{-8}$ M did not differ in levels of Mx protein expression relative to negative control. These results show a positive effect of PACAP38 on the transcription of Mx proteins at low concentrations in the range of ($10^{-9}$-$10^{-10}$ M) (FIG. 7 A). In head kidney leukocytes, the effect of PACAP 38 on the Mx protein is more moderate than in peripheral blood leukocytes, showing a stimulatory effect at a dose of $10^{-9}$ M (FIG. 7B).

Additionally, a stimulatory effect of PACAP38 was observed on the expression of TLR9, from undetectable levels of TLR9 in cultured peripheral blood leukocytes stimulated with PACAP at detectable levels in cultures stimulated with PACAP38 in the range ($10^{-10}$-$10^{-8}$ M) The highest values were obtained at a dose of $10^{-10}$ M (FIG. 8 A). In head kidney leukocytes, as it was previously observed with the Mx protein expression, the effect was more moderate. The TLR9 expression levels was statistically higher than the negative control at the intermediate dose of $10^{-9}$ M (FIG. 8 B).

IFN γ levels were undetectable in non-treated cultures of peripheral blood leukocytes. The cultures treated with 3 doses of PACAP38, resulted in detectable levels of expression with the highest level at the intermediate dose of $10^{-9}$ M (FIG. 9 A). Moreover, in cultured anterior kidney leukocytes, it was observed that PACAP38 stimulates the transcription of IFN γ. The expression levels of IFN γ were statistically higher than the control group at doses of $10^{-9}$ and $10^{-8}$ M, obtaining the best results in the highest dose of $10^{-9}$ M (FIG. 9 B).

Example 5

In Vitro Effect of the PACAP Administration in Combination with Ribavirin on IPNV Infection Supernatant from cell culture (strain ATCC VR-299) infected with IPNV as isolated viral was used. Viral confirmation was made through a specific PCR. For the in vitro assays, the cell line CHSE-214 (Chinook salmon embryo) (ECACC No 00/F1031) was used. This was maintained at 18° C. in MEM medium supplemented with Eagle salts, 10% fetal bovine serum (FBS), 2 mM glutamine and antibiotics.

The viral inoculum was grown at 15° C. and 2% FBS and before the assays the viral titer in the culture supernatant (TCID 50) was determined by the technique of Reed and Muench (Reed and Muench (1938) The American Journal of Hygiene 27: 493-497). From viral inoculum a dilution of 0.1 moi was prepared. Plates of 96-wells were seeded with CHSE-214 maintained at 18° C. in MEM (Eagle's salts) supplemented with 10% FBS, 2 mM glutamine and antibiotics. Different concentrations of ribavirin and 3 different concentrations of PACAP (0.1, 1 and 10 nM) were evaluated. At 24 hours prior to infection, cells were treated with the antiviral or the PACAP-antiviral combinations, establishing positive controls (cells infected with virus without the antiviral treatment) and negative (uninfected and untreated cells, and uninfected cells treated with the antiviral or with different doses of PACAP). Cells were infected with the viral inoculum for a period of 30 minutes of adsorption. Then the cells were washed with PBS. The treatments were diluted in MEM supplemented with 2% FBS and antibiotics and added again. The test was concluded once the cytopathic effect (CPE) in the positive control was observed. The evaluation was performed by microscopy and by staining with crystal violet (550 nm absorbance reading). The CPE in the positive control was observed at 3 days post-infection. The results of the CPE inhibition with respect to untreated and infected control cells, obtained from the absorbance values of crystal violet staining, were shown in FIG. 10. The analysis of the antiviral activity of ribavirin in combination with PACAP was performed using the program Calcusyn for Windows (Biosoft). The value of the combination index of Chou obtained showed synergism between both drugs for the concentration values tested.

Example 6

Effect of Administration of PACAP and PACAP Plus Ribavirin Combination in Rainbow Trout (*O. mykiss*) Experimentally Infected with IPNV An experiment was conducted to evaluate the effect of administration of PACAP and PACAP-ribavirin combination in rainbow trout experimentally infected with IPNV. Eight experimental groups of 50 fish each at a body weight of 1.6±0.4 g were used. The water temperature was kept at 10-12° C.

Group 1: untreated fish not exposed to the virus
Group 2: untreated fish, exposed to the virus
Group 3: Group treated with ribavirin at a dose of 400 µg/L of water, exposed to the virus
Group 4: Group treated with ribavirin at a dose of 800 µg/L of water, exposed to the virus
Group 5: Group treated with PACAP at a dose of 100 µg/L of water, exposed to the virus
Group 6: Group treated with PACAP at a dose of 200 µg/L of water, exposed to the virus.
Group 7: Group treated with the combination 1 (ribavirina 400 µg/L-PACAP 100 µg/L, exposed to the virus.
Group 8: Group treated with the combination 2 (ribavirina 800 µg/L-PACAP 200 µg/L exposed to the virus.

The animals were fed twice a day with an amount equivalent to 3% of the total corporal weight in each tank. The fish were exposed to the virus by placing them in water at 10-12° C. containing approximately $10^5$ plaque forming units (pfu)/mL of IPNV (strain ATCC VR-299) for 2 h. Fish in Groups 1 and 2 were subjected to the same stress treatment without the antiviral compound or without the PACAP-antiviral combination. The fish in Group 1 received the same procedure with cell culture medium instead of virus. The virus identification was performed by RT-PCR from kidney and spleen, according to the method described by Lopez-Lastra et al. (1994) Journal of Fish Diseases 17: 269-282. Treatments with PACAP or with PACAP-antiviral combination were performed 3 times a week for 20 days. The first treatments were performed 2 h after viral infection. Experimental observations were made during the first 20 days of treatments and 25 days after it concluded. During the experiment (45 days) deaths and abnormal behavior of the fish were monitored.

The IPNV infected fish that were not treated showed characteristic signs of infectious pancreatic necrosis from day 6 post-infection. The first death occurred on day 7 post-infection, accompanied by the worsening of the signs of the disease in all fish and a high mortality on days 11, 12 and 13 post-infection. In fish infected and treated with ribavirin or PACAP the signs of disease were detected on day 8. The groups treated with the combination ribavirin-PACAP and exposed to the virus not present signs of the disease during the period of the experiment.

The untreated and infected fish recovered appetite on day 15 post-infection. Fish treated with the antiviral recovered appetite on day 13, whereas fish treated with PACAP and PACAP-ribavirin combinations showed it on day 9 of the experiment. Fish uninfected controls showed normal behavior and there was not mortality in this group during the period of the experiment. Cumulative mortality in the untreated fish and IPNV-infected fish was 40 fish of 50 (20% survival). In fish treated with ribavirin and infected the survival was 68 and 70% for groups 3 and 4, respectively. In fish treated with PACAP and infected the survival was 50 and 55% for Groups 5 and 6, respectively. In the groups treated with the PACAP-ribavirin combinations the survival was 97 and 99% in Groups 7 and 8, respectively. In tissue samples of dead fish was found the presence of IPNV. No virus was detected in samples taken from the untreated and uninfected groups.

Table 1 shows the average weights at 45 days post-infection. Fish infected and not treated had a lower weight gain compared to uninfected fish. This weight loss was offset in the treated groups and more in the groups treated with PACAP-ribavirin combination.

TABLE 1

Increase in body weight of juvenile rainbow trout during the 45 days post-infection.

| Experimental Group | Initial Weight (g) | Final Weight (g) | Increment with respect to initial weight (%) |
|---|---|---|---|
| 1 | 1.6 ± 0.4 | 4.5 ± 1.1$^a$ | 181 |
| 2 | 1.6 ± 0.4 | 2.7 + 1.2$^b$ | 69 |
| 3 | 1.6 ± 0.4 | 3.8 ± 1.1$^c$ | 137 |
| 4 | 1.6 ± 0.4 | 3.7 ± 1.0$^c$ | 131 |
| 5 | 1.6 ± 0.4 | 5.0 ± 0.5$^d$ | 212 |
| 6 | 1.6 ± 0.4 | 5.2 ± 0.6$^d$ | 225 |
| 7 | 1.6 ± 0.4 | 5.5 ± 0.4$^d$ | 343 |
| 8 | 1.6 ± 0.4 | 5.6 ± 0.5$^d$ | 350 |

An ANOVA followed by a Tukey post test was performed. Different letters represent statistically significant differences.

Example 7

Effect of the Administration of PACAP and the PACAP Plus Ribavirin Combination Formulated in Polylactide Acid-Co-Glycolic Acid, to Rainbow Trout (*O. mykiss*) Experimentally Infected with IPNV An experiment was conducted to evaluate the effect of administration of PACAP and PACAP-ribavirin combination contained in polylactic acid-co-glycolic acid (PLGA) to rainbow trout experimentally infected with IPNV. Eight experimental groups were performed of 30 fish of 30±4 g each one and were kept in water at 10-12° C.:
Group 1: fish injected with PLGA, not exposed to the virus
Group 2: fish injected with PLGA exposed to the virus
Group 3: Group injected with ribavirin at a dose of 4 µg/g of fish, exposed to the virus Group 4: Group injected with ribavirin at a dose of 8 μg/g of fish, exposed to the virus
Group 5: Group PACAP injected at a dose of 0.1 μg/g of fish, exposed to the virus
Group 6: Group PACAP injected at a dose of 0.2 μg/g of fish exposed to the virus
Group 7: Group injected with the combination 1 (ribavirin 4 μ/g-PACAP 0.1 μg/g), exposed to the virus
Group 8: group injected with the combination 2 (ribavirin 8 μg/g-PACAP 0.2 μg/g), exposed to the virus Nanoparticles containing PACAP or PACAP-ribavirin combination, were administered by intraperitoneal injection 2 hours after viral infection. Experimental observations were conducted for 30 days. Results on survival rates similar to those described in Example 6 were obtained.

Example 8

Effect of Administration of PACAP and the PACAP Plus Ribavirin Combination in Atlantic Salmon (*Salmo salar*) Experimentally Infected with IPNV An experiment was conducted to evaluate the effect of the administration of PACAP and PACAP-ribavirin combination for salmon (*Salmo salar*) experimentally infected with IPNV. Eight experimental groups were performed of 50 fish and a size of 1.2±0.3 g each one and were kept in water at 10-12° C.:
Group 1: untreated fish not exposed to the virus
Group 2: untreated fish, exposed to the virus
Group 3: Group treated with ribavirin at a dose of 400 μg/L of water, exposed to the virus
Group 4: Group treated with ribavirin at a dose of 800 μg/L of water, exposed to the virus
Group 5: Group treated with PACAP at a dose of 100 μg/L of water, exposed to the virus
Group 6: Group treated with PACAP at a dose of 200 μg/L, exposed to the virus
Group 7: Group treated with ribavirin 400 μg/L-PACAP 100 μg/L combination, exposed to the virus
Group 8: Group treated with ribavirin 800 μg/L-PACAP 200 μg/L combination, exposed to the virus.

The animals were fed twice a day with an amount equivalent to 3% of the total corporal weight in each tank. The fish were exposed to the virus by placing them in water at 10-12° C. containing approximately $10^5$ pfu/mL of IPNV (strain ATCC VR-299) for 2 h. Treatments were performed 3 times a week for 20 days. Experimental observations were made during this period and 25 days after the last treatments. During the 45 days of the experiment deaths and abnormal behavior of the fish were monitored. Fish in Groups 1 and 2 were subjected to the same stress produced by the treatment without the antiviral compound or the combination of PACAP-antiviral. The fish in Group 1 received the same procedure with cell culture medium instead of the virus. The identification of the virus was performed by RT-PCR from kidney and spleen, according to the method described by López-Lastra et al. (1994) Journal of Fish Diseases 17: 269-282.

The fish infected with IPNV and not treated showed characteristic signs of infectious pancreatic necrosis from day 6 post-infection. The first death occurred on day 8 post-infection, accompanied by the worsening of the signs of the disease in all fish and a high mortality between day 11 and 15 post-infection. The percentage of survival in this group was 30%. There was a loss of appetite on days 10 and 11 in all groups infected with the virus, with the exception of the groups treated with PACAP, PACAP-ribavirin combination and the uninfected group. In fish infected and treated with both doses of ribavirin early signs of disease were detected on day 10 and there was a 70-76% survival for the low and high doses, respectively. In fish infected and treated with PACAP the survival was a 56-60% for the low and high doses, respectively. In the group treated with the combination ribavirin-PACAP and exposed to the virus the survival was a 96-98%. In the uninfected and untreated group the percentage of survival was 98%. In tissue samples of dead fish was found the presence of IPNV.

Table 2 shows the average weights at 45 days post-infection. Fish infected and untreated had a lower weight gain compared to uninfected fish. This weight loss was offset in the treated groups and more in the groups treated with PACAP and PACAP-ribavirin combinations.

TABLE 2

Increase in body weight of juvenile Atlantic salmon during the 45 days post-infection.

| Experimental Group | Initial Weight (g) | Final Weight (g) | Increment (%) |
| --- | --- | --- | --- |
| 1 | 1.2 ± 0.3 | 2.5 ± 0.8$^a$ | 108 |
| 2 | 1.2 ± 0.3 | 2.0 ± 0.4$^b$ | 67 |
| 3 | 1.2 ± 0.3 | 2.2 ± 0.4$^c$ | 83 |
| 4 | 1.2 ± 0.3 | 2.3 ± 0.5$^c$ | 92 |
| 5 | 1.2 ± 0.3 | 2.4 ± 0.3$^a$ | 200 |
| 6 | 1.2 ± 0.3 | 2.8 ± 0.3 | 233 |
| 7 | 1.2 ± 0.3 | 3.1 ± 0.2 | 258 |
| 8 | 1.2 ± 0.3 | 3.4 ± 0.1 | 283 |

An ANOVA followed by a Tukey post test was performed. Different letters represent statistically significant differences.

Example 9

Effect of Administration of PACAP and PACAP Plus Ribavirin Combination in Atlantic Salmon (*Salmo salar*) Experimentally Infected with ISAV An experiment was conducted to evaluate the effect of the administration of PACAP and PACAP-ribavirin combination for salmon (*Salmo salar*) experimentally infected with ISAV. Eight experimental groups were performed of 25 fish and 50±10 g each one. The groups were kept in sea water at 10-12° C.
Group 1: Fish untreated, not exposed to the ISA virus
Group 2: untreated fish, exposed to the ISA virus
Group 3: Group treated with ribavirin at a dose of 400 μg/L of water, exposed to the virus
Group 4: Group treated with ribavirin at a dose of 800 μg/L of water, exposed to the virus
Group 5: Group treated with PACAP at a dose of 100 μg/L of water, exposed to the virus
Group 6: Group treated with PACAP at a dose of 200 μg/L of water, exposed to the virus
Group 7: Group treated with the combination of ribavirin 400 μg/L-PACAP 100 μg/L, exposed to the virus
Group 8: Group treated with the combination of ribavirin 800 μg/L-PACAP 200 μg/L, exposed to the virus To obtain sufficient virus for the challenge experiments were cultured SHK-1 cells and infected with the strain Glesvaer (access No. AJ012285, Krossoy et al. (1999) Journal of Virology 73: 2136-2142) in 175 cm$^2$ flasks for 5 days.

Fish were exposed to the virus by cohabitation with fish injected intraperitoneally with 0.3 mL of culture medium containing approximately $10^4$ pfu/mL of ISAV. Group 1: fish that received an equal volume of culture medium. The % of mortality in Group 1 (untreated, not exposed to the virus ISA) was 4% and in Group 2 (exposed to virus and untreated) was 92%. In the Groups 3 and 4, mortality was 52 and 36%, respectively while in Groups 5 and 6 was 60 and 72%, respectively. In Groups 7 and 8 treated with PACAP-ribavirin combination the % of mortality was 8 and 4%, respectively. In tissue samples of dead fish was found the presence of ISAV. No virus was detected in samples from untreated and uninfected group.

Example 10

Effect of the Administration of PACAP and PACAP-amantadine Combination on Rainbow Trout (*O. mykiss*) Experimentally Infected with IHNV An experiment was conducted to evaluate the effect of the administration of PACAP and PACAP-amantidine combination in rainbow trout experimentally infected with IHNV. Eight experimental groups were performed of 50 fish of 50±5 g each one and were kept in water at 10-12° C.
Group 1: untreated fish not exposed to the virus
Group 2: untreated fish, exposed to the virus
Group 3: Group treated with amantadine at a dose of 400 µg/L of water, exposed to the virus
Group 4: Group treated with amantadine at a dose of 800 µg/L of water, exposed to the virus
Group 5: Group treated with PACAP at a dose of 100 µg/L of water, exposed to the virus
Group 6: Group treated with PACAP at a dose of 200 µg/L of water exposed to the virus
Group 7: Group treated with the combination 1 (amantidina 400 µg/L-PACAP 100 µg/L exposed to the virus
Group 8: Group treated with the combination 2 (amantidina 800 µg/L-PACAP 200 µg/L exposed to the virus The experimental conditions were similar to the experiments described in the previous examples. The fish were challenged by immersion with $5.9 \times 10^3$ pfu/ml virus in 20 L of water with aeration for 1 hour. As a result of the experiment a survival of a 26% was observed in the untreated and infected fish with IHNV. In fish treated with amantadine and infected with IHNV the survival was 46%. In fish treated with PACAP and infected with IHNV the survival was 36%. In the groups treated with the PACAP-amantidine combination the survival was 96-98%.

Example 11

Effect of the Administration of PACAP and the PACAP Plus Ribavirin Combination on Pacific White Shrimp (*Litopenaeus vannamei*) Experimentally Infected with the Virus of White Spot Syndrome (WSSV)

An experiment was conducted to evaluate the effect of the administration of PACAP and PACAP-ribavirin combination on Pacific white shrimp *Litopenaeus vannamei* experimentally infected with WSSV. Four experimental groups were formed of 50 shrimp of 5±0.5 g each one and were kept in seawater at 28° C.:

The shrimp were fed twice a day with an amount equivalent to 8% of the total biomass per group. The experimental groups were:
Group 1: untreated, not exposed to the virus WSSV
Group 2: untreated, exposed to the virus WSSV
Group 3: Treated with ribavirin, exposed to the virus WSSV
Group 4: Treated with PACAP, exposed to the virus WSSV
Group 5: treated with the combination ribavirin-PACAP, exposed to the virus WSSV For the isolation and viral spread was used *Orconectes limosus* crab. WSSV was purified from freshly extracted hemolymph by sucrose gradient centrifugation as described by Van Hulten et al in 2001 (Van Hulten et al. (2001) Virology 285: 22833).

The viral samples were stored at −80° C. until use.

In order to minimize the natural routes of infection with WSSV and to achieve reproducible protocol the immersion via was used to induce the experimental viral infection. Prior to the viral infection the viral titer and the amount required to cause 75% mortality was determined. To do that the shrimp were experimentally infected with different dilutions of the virus during an incubation period of 7 hours.

Following the viral infection, shrimps were washed with seawater free of virus and placed in new containers according to the design of the experimental groups described above.

The treatments were administered 3 times per week for 30 days at a dose of (500 µg of antiviral/L of water) or (500 µg of antiviral plus PACAP 200 µg/L of water), post-infection. For the group treated with PACAP the used dose was of 200 µg/L of water. Shrimp in Groups 1 and 2 were subjected to the same stress of treatments administration. During the 30 days of the experiment deaths in each experimental group were monitored.

The % of mortality in the Group 2 (untreated, exposed to the virus) was 60% in Group 1 (untreated, not exposed to the virus) was 0% in Group 3 (treated with ribavirin, exposed virus) mortality was 16%, while the PACAP treated group mortality was 26%. In the group treated with PACAP-ribavirin combination % mortality was 2%. In tissue samples of dead shrimp were detected WSSV by RT-PCR.

Example 12

Effect of Administration of PACAP and the PACAP Plus Ribavirin Combination in Oysters of the Species *Pecten maximus* Experimentally Infected with IPNV An experiment was conducted to evaluate the effect of administration of PACAP and PACAP-ribavirin combination in oysters of the species *Pecten* maximus experimentally infected with IPNV. Eight experimental groups were performed of 30 adult oysters each one and were kept in 250 L of filtered sea water at 10° C. No virus was detected in hepatopancreas samples collected prior to the start of the experiment. The experimental groups were:
Group 1: untreated, not exposed to the virus
Group 2: untreated, exposed to the virus
Group 3: Group treated with ribavirin at a dose of 400 µg/L of water, exposed to the virus
Group 4: Group treated with ribavirin at a dose of 800 µg/L of water, exposed to the virus
Group 5: Group treated with PACAP at a dose of 100 µg/L of water, exposed to the virus
Group 6: Group treated with PACAP at a dose of 200 µg/L of water exposed to the virus Group 7: Group treated with the combination 1 (ribavirina 400 μg/L-PACAP 100 μg/L exposed to the virus
Group 8: Group treated with the combination 2 (ribavirina 800 μg/L-PACAP 200 μg/L exposed to the virus Treatments were performed 3 times a week for 20 days. Oysters were challenged by exposure to 25 L of water containing $10^7$ TCID50 mL$^{-1}$ in tanks of 80 L. After 6 h the water was replaced at a slow flow of 1 L/min and at 12 h the flow was increased to 3 L/min.

Two weeks after challenge hepatopancreas samples were taken and determined the viral titer. The results showed a decrease in viral load in animals treated with ribavirin and PACAP. This decrease was greater in the groups treated with the combination (Table 3).

TABLE 3

IPNV average viral titer ($\log_{10}$TCID50 g$^{-1}$) in the hepatopancreas of oysters two weeks after the challenge. Different letters indicate significant differences.

| Groups | Viral Titer |
| --- | --- |
| 1 | 0 |
| 2 | 8.1$^a$ |
| 3 | 5.4$^b$ |
| 4 | 4.3$^b$ |
| 5 | 6.5$^c$ |
| 6 | 5.8$^c$ |
| 7 | 2.0$^d$ |
| 8 | 1.5$^d$ |

The invention claimed is:

1. A method for the treatment of viral infections and infectious diseases caused by viruses in aquatic organisms comprising administering Pituitary Adenylate Cyclase Activating Polypeptide (PACAP) to aquatic organisms, wherein aquatic organisms are selected from the group consisting of fish, crustaceans, and bivalves.

2. The method of claim 1 wherein the PACAP is obtained a) by isolation from its natural source, b) synthetically, or c) by recombinant DNA technology.

3. The method of claim 2 wherein the PACAP is isolated from fish.

4. The method of claim 1 wherein the fish are salmonids, and the crustaceans are penaeid shrimps.

5. The method of claim 1 wherein the PACAP is used in the therapeutic treatment of viral infections caused by viruses, wherein the viruses are selected from the group consisting of Herpesviridae, Papovaviridae, Togaviridae, Retroviridae, Reoviridae, Birnavirida, and Picornaviridae families.

6. The method of claim 1 further comprising administering an antiviral molecule selected from the group consisting of ribavirin, a ribavirin analog, 5-ethynyl-1-β-D-ribofuranosylimidazole-carboxamide, and amantadine.

7. The method of claim 6 wherein the PACAP and the antiviral molecule are administered simultaneously, separately, or sequentially during the same treatment.

8. The method of claim 6 wherein the PACAP and the antiviral molecule are administered orally, by injection or by immersion bath.

9. The method of claim 8 wherein the PACAP and antiviral molecule are part of a formulated feed, wherein the PACAP is at a concentration of 50-750 μg/kg of feed and the antiviral molecule is at a concentration of 100-2000 μg/kg of feed.

10. The method of claim 8 wherein the PACAP and antiviral molecule are administered by injection, wherein the PACAP is at a concentration of 0.1-10 μg/gbw (gram of body weight) and the antiviral molecule at a concentration of 1-50 μg/gbw.

11. The method of claim 8 wherein the PACAP and antiviral molecule are administered by immersion bath, wherein the PACAP is at a concentration of 50-1000 μg/L of water and the antiviral molecule is at a concentration of 100-2000 μg/L of water.

* * * * *